(12) United States Patent
Johnson

(10) Patent No.: US 8,470,022 B2
(45) Date of Patent: *Jun. 25, 2013

(54) IMPLANTABLE VALVE

(75) Inventor: Chad E. Johnson, West Lafayette, IN (US)

(73) Assignee: Cook Biotech Incorporated, West Lafayette, IN (US)

( * ) Notice: Subject to any disclaimer, the term of this patent is extended or adjusted under 35 U.S.C. 154(b) by 573 days.

This patent is subject to a terminal disclaimer.

(21) Appl. No.: 11/513,881

(22) Filed: Aug. 31, 2006

(65) Prior Publication Data
US 2007/0050014 A1    Mar. 1, 2007

Related U.S. Application Data

(60) Provisional application No. 60/712,990, filed on Aug. 31, 2005.

(51) Int. Cl.
*A61F 2/24* (2006.01)

(52) U.S. Cl.
CPC .................................. *A61F 2/2475* (2013.01)
USPC ........... 623/1.24; 623/1.26; 623/2.14; 600/36

(58) Field of Classification Search
USPC ................ 623/2.13, 2.14, 2.17, 1.24; 600/36
See application file for complete search history.

(56) References Cited

U.S. PATENT DOCUMENTS

| | | | |
|---|---|---|---|
| 3,514,791 A * | 6/1970 | Sparks | 623/2.13 |
| 4,218,782 A | 8/1980 | Rygg | |
| 4,319,363 A | 3/1982 | Ketharanathan | |
| 4,902,508 A | 2/1990 | Badylak et al. | |
| 4,956,178 A | 9/1990 | Badylak et al. | |
| 5,156,620 A | 10/1992 | Pigott | |
| 5,281,422 A | 1/1994 | Badylak et al. | |
| 5,411,552 A | 5/1995 | Andersen et al. | |
| 5,489,297 A * | 2/1996 | Duran | 623/2.13 |
| 5,554,389 A | 9/1996 | Badylak et al. | |
| 5,607,465 A | 3/1997 | Camilli | |
| 5,855,601 A | 1/1999 | Chuter et al. | |
| 5,955,110 A | 9/1999 | Patel et al. | |
| 6,099,567 A | 8/2000 | Badylak et al. | |
| 6,110,201 A | 8/2000 | Quijano et al. | |
| 6,126,686 A | 10/2000 | Badylak et al. | |
| 6,168,614 B1 | 1/2001 | Andersen et al. | |
| 6,200,336 B1 | 3/2001 | Pavcnik et al. | |
| 6,206,931 B1 | 3/2001 | Cook et al. | |
| 6,241,763 B1 * | 6/2001 | Drasler et al. | 623/1.24 |
| 6,287,334 B1 | 9/2001 | Moll et al. | |
| 6,299,637 B1 | 10/2001 | Shaolian et al. | |
| 6,352,555 B1 | 3/2002 | Dzau et al. | |
| 6,454,799 B1 * | 9/2002 | Schreck | 623/2.18 |

(Continued)

FOREIGN PATENT DOCUMENTS

| WO | WO 00/23008 | 4/2000 |
|---|---|---|
| WO | WO 01/19285 | 3/2001 |

(Continued)

*Primary Examiner* — Thomas J Sweet
*Assistant Examiner* — Megan Wolf
(74) *Attorney, Agent, or Firm* — Woodard, Emhardt, Moriarty, McNett & Henry LLP

(57) ABSTRACT

Described are implantable prosthetic valve devices comprising isolated granulation tissue. Also described are methods of treatment that include implanting at least one of these valves within a body passageway of a patient, for example, within a vein to treat venous insufficiency.

27 Claims, 5 Drawing Sheets

U.S. PATENT DOCUMENTS

| | | |
|---|---|---|
| 6,475,232 B1 | 11/2002 | Babbs et al. |
| 6,508,833 B2 | 1/2003 | Pavcnik et al. |
| 6,582,462 B1 | 6/2003 | Andersen et al. |
| 6,626,823 B1 * | 9/2003 | Campbell et al. ............... 600/36 |
| 6,716,241 B2 | 4/2004 | Wilder et al. |
| 6,752,828 B2 | 6/2004 | Thornton |
| 7,815,923 B2 * | 10/2010 | Johnson et al. ............... 424/400 |
| 2001/0011187 A1 | 8/2001 | Pavcnik et al. |
| 2001/0039450 A1 | 11/2001 | Pavcnik et al. |
| 2002/0094573 A1 * | 7/2002 | Bell ............................. 435/398 |
| 2002/0123800 A1 | 9/2002 | Taheri et al. |
| 2002/0188348 A1 | 12/2002 | DiMatteo et al. |
| 2003/0036795 A1 | 2/2003 | Andersen et al. |
| 2003/0130726 A1 | 7/2003 | Thorpe |
| 2003/0191525 A1 | 10/2003 | Thornton |
| 2003/0208261 A1 | 11/2003 | Thorpe et al. |
| 2004/0015230 A1 | 1/2004 | Moll et al. |
| 2004/0024452 A1 * | 2/2004 | Kruse et al. .................. 623/2.13 |
| 2004/0049262 A1 | 3/2004 | Obermiller et al. |
| 2004/0106991 A1 * | 6/2004 | Hopkins et al. .............. 623/2.13 |
| 2004/0126404 A1 | 7/2004 | Campbell et al. |
| 2004/0193253 A1 | 9/2004 | Thorpe et al. |
| 2005/0267560 A1 | 12/2005 | Bates |

FOREIGN PATENT DOCUMENTS

| | | |
|---|---|---|
| WO | WO 01/37884 | 5/2001 |
| WO | WO 03/070124 | 8/2003 |
| WO | WO 03/092471 | 11/2003 |
| WO | WO 2004/082528 | 9/2004 |
| WO | WO 2005/011534 | 2/2005 |
| WO | WO 2005/089673 | 9/2005 |

\* cited by examiner

IMPLANTABLE VALVE

STATEMENT OF RELATED APPLICATIONS

This application claims the benefit of priority of U.S. Provisional Patent Application Ser. No. 60/712,990 filed Aug. 31, 2005, which is incorporated herein by reference in its entirety.

BACKGROUND

The present invention relates generally to medical devices and methods and in particular aspects to implantable valve devices comprising isolated granulation tissue.

It is well understood in human pathology that the proper functioning of cardiac and venous valves is of the utmost importance. Numerous studies have shown that diseased cardiac valves cause significant morbidity and mortality and that incompetent or damaged venous valves often result in adverse medical conditions, especially in the lower extremities.

By preventing retrograde blood flow, the valves found throughout the venous system assist the flow of blood through the veins and returning to the heart. Venous valves are usually of the bicuspid type, with each cusp or leaflet forming a reservoir for blood, which, under pressure, forces the free edges of the cusps together to permit mostly antegrade blood flow to the heart. As a majority of venous blood flow is against gravity while a person is standing, incompetent or damaged venous valves can cause significant medical problems in the legs, ankles, and feet. There are at least two chronic venous diseases in which venous valve incompetence is thought to be an important factor: chronic venous insufficiency and varicose vein syndrome.

Chronic venous insufficiency involves venous hypertension and chronic venous stasis due to valvular incompetence. It has been estimated that in the United States chronic venous insufficiency associated with skin changes and ulcers affects six to seven million people. Varicose vein syndrome involves vein dilation or enlargement. According to another estimate, varicose veins affect about 4% of the adult western population, and approximately half of this population has significant varicose vein syndrome for which treatment will be sought.

Turning now to the cardiovascular system, incompetent or destroyed heart valves are a common form of heart disease, the leading cause of death in the United States. Although reconstructive surgery has been shown to be superior to valve replacement surgery in some respects, it is difficult to perform and not always possible in every patient. As a result, the vast majority of patients with diseased heart valves undergo valve replacement surgery, which involves removing a native valve and replacing it with a prosthetic one. Prosthetic heart valves come in various shapes and sizes and can be formed with a variety of materials. Often, the design of a prosthetic valve depends on the characteristics of the valve being replaced (e.g., mitral, aortic, tricuspid, or pulmonary) and/or the size of the patient's heart.

A variety of prosthetic valves have been developed in the art to treat conditions of the vascular system. For example, U.S. Pat. No. 6,508,833 discloses a multiple-sided medical device comprising a closed frame of a single piece of wire or other resilient material and having a series of bends and interconnecting sides. The device has both a flat configuration and a second, folded configuration that comprises a self-expanding frame. The device is pushed from a delivery catheter into the lumen of a duct or vessel. A covering of fabric or other flexible material is sutured or attached to the frame to form an artificial valve. The flexible material utilized in the disclosed valves can be comprised of collagenous submucosa obtained from various animals, such as, for example, pigs, cattle, and sheep. The submucosal material can be prepared in large, flat sheets, which are subsequently cut and attached to a framing element, for example a stent, for deployment in a vein.

There remain needs for improved and/or alternative prosthetic valves, as well as methods of using the same to treat conditions of the vascular system. The present invention is addressed to those needs.

SUMMARY

The present invention provides, in certain aspects, unique medical valve leaflets that include tissue, wherein the tissue is formed in a body location other than where the leaflets are to be implanted. In some embodiments, the tissue is formed on a three-dimensional mold or other suitable device. Illustratively, certain aspects of the present invention relate to prosthetic valve implants comprising isolated granulation tissue, wherein the granulation tissue is formed in a body cavity, and the valves are configured for implantation within a tubular body passageway. For example, a valve adapted for implantation within a vascular vessel (e.g., a vein) can comprise isolated granulation tissue formed in a peritoneal cavity. In certain preferred aspects, the body cavity is in the patient being treated, making the isolated granulation tissue autologous relative to the implant recipient, although such is not necessary to broader aspects of the invention.

In one particular embodiment, the invention provides an implantable valve for modifying fluid flow in a body passageway, the valve comprising isolated granulation tissue. In certain preferred aspects, the isolated granulation tissue is formed in a body cavity of a human, and the valve is configured for implantation within a body passageway of that same human. The isolated granulation tissue can include cells obtained in the body cavity including but not limited to mesothelial cells, macrophages, and myofibroblasts. The valve can have any suitable number of leaflets, e.g., one, two, three, or more leaflets, and may optionally be associated with one or more frame elements. The valve can be configured for implantation as a vascular valve. For example, in some aspects, the valve is configured for implantation as a heart valve, while in other aspects, the valve is configured for implantation as a venous valve. Also, the valve may include adaptations for attaching the valve to walls of a body passageway.

Another embodiment of the present invention provides a method of forming an implantable valve cusp such as that described above, wherein the method comprises inserting a cusp-forming device into a body cavity, and removing the cusp-forming device from the body cavity after tissue, e.g., granulation and/or other tissue, has formed thereon. In certain aspects, the method also comprises manipulating the cusp-forming device and/or the tissue formed thereon, or any portions thereof, as part of providing an implantable valve cusp. Suitable manipulation can include, for example, separating at least a portion of the tissue from the cusp-forming device, or otherwise chemically, biologically, and/or physically altering the device and/or tissue, or any portions thereof. For example, in some aspects, the tissue that is formed is decellularized after it is removed from the body cavity or before it is implanted. Any suitable body cavity can be used in the invention including but not limited to a peritoneal cavity. Also, the cusp-forming device may be inserted into and/or removed from the body cavity using any suitable technique and/or instrumentation, e.g., laparoscopically and/or in an open surgery. The cusp-forming device can be formed with a variety of materials, such as but not limited to, a metallic material, a ceramic material, and/or a synthetic polymeric material. In certain aspects, the cusp-forming device comprises a mold and/or a frame, either of which may or may not be retained as part of the implantable valve provided for implantation.

In yet another embodiment, the invention provides a medical product that comprises at least one implantable valve such as that described above contained in a sealed package. In certain aspects, the at least one valve is configured for implantation in a body passageway having a predetermined inner diameter. In other aspects, the at least one valve is configured for implantation in body passageways having various predetermined inner diameters. Also, the product can include suitable instrumentation for implanting the at least one valve within a body passageway. Further, the sealed package can be configured to maintain the at least one valve in a sterile condition when sterilely packaged therein, and can include indicia to communicate the contents of the package.

In another embodiment, the invention provides a method of treatment that comprises implanting at least one valve such as that described above within a body passageway of a patient. For example, in certain preferred aspects, the at least one valve is implanted within a vascular vessel to treat venous insufficiency. Any suitable technique and/or instrumentation may be used to implant or engraft the at least one valve within the passageway including but not limited to percutaneously with a delivery device such as a catheter.

Other objects, embodiments, forms, features, advantages, aspects, and benefits of the present invention shall become apparent from the detailed description and drawings included herein.

DETAILED DESCRIPTION

Figure 1:
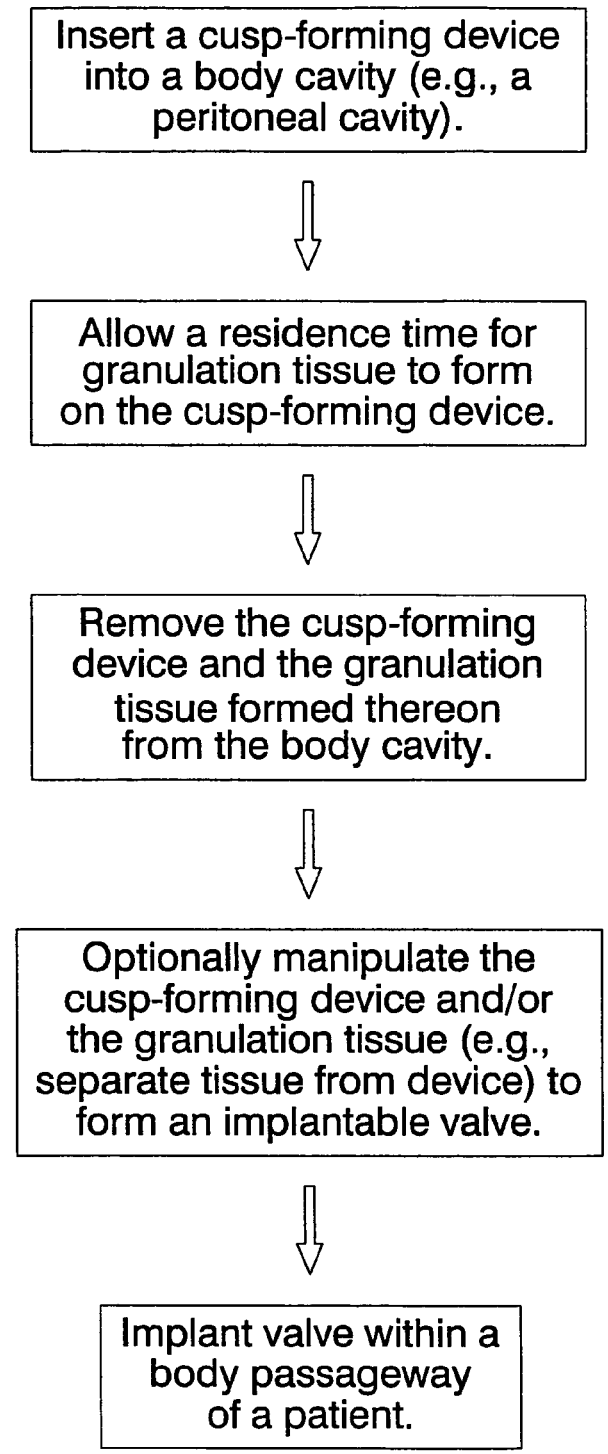
FIG. 1 provides a flow chart depicting one embodiment of the present invention for treating a condition of the vascular system.

While the present invention may be embodied in many different forms, for the purpose of promoting an understanding of the principles of the present invention, reference will now be made to the embodiments illustrated in the drawings, and specific language will be used to describe the same. It will nevertheless be understood that no limitation of the scope of the invention is thereby intended. Any alterations and further modifications in the described embodiments and any further applications of the principles of the present invention as described herein are contemplated as would normally occur to one skilled in the art to which the invention relates.

Valve prosthesis devices can be used to replace and/or supplement incompetent or damaged cardiac or venous valves in mammals or to otherwise beneficially modify fluid flow in a bodily passage. The present invention, illustrative examples of which are shown in FIGS. 1-4, provides improved and/or alternative prosthetic valves that can be implanted within a tubular body passage of a patient, especially a human, including for example in veins or arteries.

With reference now to FIG. 1, shown is a flow chart depicting an embodiment of the present invention for treating a patient. As described in greater detail below, this illustrative embodiment includes forming a prosthetic valve device comprising isolated granulation tissue, and thereafter implanting the valve within a body passageway. In this regard, implanting a prosthetic valve in accordance with the present invention avoids having to sacrifice existing, i.e. indigenous, tissue from the implant recipient.

As illustrated in FIG. 1, one step of the method includes inserting a cusp-forming device into a body cavity. Any suitable body cavity may be utilized in the invention including but not limited to the peritoneum, thoracic cavity, scrotum, brain, joint or pericardial cavity. In certain preferred aspects of the invention, the body cavity is lined with mesothelial cells. The peritoneal cavity is preferred in some forms of the invention, because it is relatively easy to access and generally considered less-disruptive to the host.

Insertion of the cusp-forming device can be accomplished in any suitable manner. In this regard, any suitable invasive, non-invasive, or minimally invasive technique and/or instrumentation can be employed. For example, in certain embodiments, a cusp-forming device is inserted into a body cavity laparoscopically, while in other embodiments, the same is accomplished via open surgery. The cusp-forming device may be inserted into the body cavity so that it is generally placed without restraint in the cavity, i.e., it is "free floating." Alternatively, the device can be fixed to a region within the body cavity, which may make insertion and/or removal of the device easier.

The cusp-forming device can have any suitable size, shape, and/or configuration to provide material for a cusp suitable for implantation within a body passageway. For example, the device could be generally planar, or it could have non-planar portions, e.g., concave or convex portions. Alternatively, the cusp-forming device can be associated with one or more other body cavity-insertable elements, such as but not limited to, a frame, a container, and/or the like, wherein any of these elements may comprise a biodegradable matrix. For example, in certain aspects, a cusp-forming device is placed inside a container before being inserted (or as it is being inserted) into a body cavity. In these embodiments, at least a portion of the container may be perforated to allow passage of cells and growth factors therethrough. In other aspects, a cusp-forming device is associated with one or more frame elements, any of which may or may not be retained as part of the implantable valve provided for implantation.

After being inserted therein, the cusp-forming device is kept in the body cavity for a period of time sufficient for granulation tissue to form thereon. (Hereinafter, this period of time will be referred to as a "residence time."). The cusp-forming device constitutes a foreign object inside the body cavity. In certain embodiments, the cusp-forming device is configured to provoke an inflammatory response, thereby leading to the formation of granulation tissue thereon. This granulation tissue can include cells involved in an immune-mediated inflammatory response. For example, the granulation tissue can include granulocytes, macrophages, and/or stromal cells. Such tissue can also include myofibroblasts and/or mesothelial cells.

The shape and/or configuration of the cusp-forming device influences the shape and/or configuration of the granulation and/or other tissue formed. In this regard, granulation tissue can form on, around, or inside the cusp-forming device, or any portion thereof, or can otherwise be incorporated into or engaged with the device in some manner. Accordingly, the granulation tissue generally takes the form of the shape of the cusp-forming device, or portions thereof. Certain embodiments have at least a region with a convexo-concave shape, i.e., concave on one side and convex on the other. In some aspects, the body cavity is in the patient being treated, making at least a portion of the isolated granulation tissue material autologous relative to the recipient of the valve implant prosthesis.

The residence times of the present invention can be varied depending on any number of factors, including but not limited to, the amount of granulation tissue predicted to form on the device after a certain amount of time and/or under a particular set of conditions and/or circumstances. It should be noted that various residence time schedules can be designed through routine experimentation so as to allow for a suitable amount of granulation tissue formation. In certain preferred aspects, the cusp-forming device is left inside the body cavity for at least 1 week but no longer than 12 weeks, more typically for at least 2 weeks but no longer than 6 weeks, although it is to be understood that such residence time schedules are not necessary to broader aspects of the invention. Advantageous residence time schedules of the invention are those that allow for the formation of an essentially continuous sheet of granulation tissue from which to form a valve cusp of the invention, or a portion thereof.

After a proper residence time, the cusp-forming device is removed from the body cavity. Any suitable instrumentation and/or technique may be used to remove the device, including but not limited to those herein disclosed for inserting the device.

After being removed from the body cavity, the cusp-forming device and/or the granulation tissue formed thereon are optionally manipulated to form a prosthetic cusp suitable for implantation within a body passageway. The device-tissue combination can be manipulated in any suitable manner, including but not limited to, cleaning, sterilizing, and/or performing any manner of chemical, biological, and/or physical alteration of, the device and/or tissue, or any portions thereof. For example, in certain preferred embodiments, manipulation includes separating the granulation tissue, or portions thereof, from the device. In these embodiments, the separated tissue material, or portions thereof, can then be adapted for implantation as one or more prosthetic cusps. Any suitable technique and/or instrumentation can be used to separate the tissue from the form, such as but not limited to cutting with a scalpel. In certain embodiments, especially those involving granulation or other formed tissue that is allogenic or xenogenic relative to the patient receiving the implant, the tissue is decellularized after it is removed from the body cavity or before it is implanted. Additionally, in some forms, prosthesis materials are disinfected or sterilized before they are implanted in a patient, for example, as described in U.S. Pat. No. 6,206,931, which is hereby incorporated by reference in its entirety.

A prosthetic cusp of the invention can be adapted to provide any prosthetic valve device suitable for implantation within a body passageway of a patient, wherein these valves may or may not include one or more frame elements. For example, a prosthetic cusp of the invention can be adapted to provide a monocusp valve in a vascular vessel, or, alternatively, a plurality of prosthetic cusps can be adapted to provide for a multicuspid valve in a vascular vessel, wherein the multicuspid valve comprises a plurality of cusps. In this respect, a plurality of prosthetic cusps can be adapted to provide a bicuspid valve, a tricuspid valve, or a quadracuspid valve in a vascular vessel.

When a monocusp valve configuration is utilized in the invention, the cusp can be dimensioned and attached to the vessel in such a manner so as to allow the cusp to extend across the entire lumen of a vessel and co-apt with or otherwise desirably contact the opposite wall of the vessel. Alternatively, two or more prosthetic cusps can be provided and dimensioned for separate attachment to the wall of the vessel so as to co-apt with each other within the vessel lumen, e.g. near the middle of the lumen. When a multicusp valve configuration is utilized, the valve can comprise at least two cusps, wherein the at least two cusps are attached to the vessel wall in such a manner so as to allow the cusps to co-apt within the lumen of the vessel, e.g. near the center of the lumen of the vessel.

Advantageous configurations are those that result in a net increase in blood flow in the native flow direction. In certain aspects of the invention, the valve configuration is such that fluid flow through the valve in the native flow direction passes through a co-apt region within the valve, e.g., an area where a monocusp contacts or nearly contacts the opposite wall of a vessel or where at least two cusps contact or nearly contact each other within the lumen of the vessel, e.g., near the center of the lumen, while fluid flow in the opposite direction is restricted.

A number of potential attachment paths are contemplated as within the scope of the present invention. For example, the edges of the cusp(s) can extend in a direction generally both longitudinally and circumferencially around the vessel wall. Also, the cusp(s) can be attached to the vessel wall in any suitable manner including but not limited to utilizing mechanical elements, sutures, bonding, welding, or the like.

Further in this regard and whether or not still attached to the cusp-forming device, the granulation tissue, or portions thereof, can be associated with one or more frame elements before or after being implanted within a body passageway. For example, one or more prosthetic cusps could be associated with one or more removable frame elements as described in International Patent Application serial No. PCT/US2004/008176 filed Mar. 17, 2004, published Sep. 30, 2004, as WO2004/082528, which is hereby incorporated by reference. In this manner, a valve construct including the removable frame element(s) and cusp(s) can be implanted (e.g. percutaneously) in a bodily passageway of a patient, such as a vein or artery, allowed to indwell for a sufficient period of time to achieve tissue ingrowth into the valve (e.g. for site fixation and/or sealing), and the removable frame element(s) thereafter retrieved (e.g. percutaneously). The resulting long-term valve in the patient can thereby include fewer or no associated frame elements.

Additionally, a prosthetic cusp of the present invention may include one or more adaptations to suitably anchor the same within a body vessel. For example, one or more vessel-attaching elements (e.g., barbs) can be attached to or incorporated into the cusp to attach the same to a vessel wall. In addition to barbs, suitable adaptations can include any suitable device or material such as but not limited to adhesives, hooks, and the like. Also, these adaptations can be associated with the prosthetic cusp before or after the same is implanted within the vessel.

Continuing with FIG. 1, the illustrative embodiment further includes implanting the prosthetic cusp within a body passageway as a method of treatment. Implantation can be accomplished in any suitable manner including but not limited to percutaneously or via open surgery. In certain preferred embodiments, a prosthetic cusp is implanted or engrafted within a venous vessel to treat venous reflux.

Suitable isolated granulation tissue material can include xenografts (i.e., cross species, such as a non-human donor for a human recipient), allografts (i.e., interspecies with a donor of the same species as the recipient) and/or autografts (i.e., the donor and the recipient being the same individual). Illustratively, a prosthetic valve device of the invention can comprise autologous tissue. For example, in certain preferred embodiments, a cusp-forming device is inserted into a body cavity of a human host. After granulation tissue has formed on the device, the device is removed from the body cavity. Thereafter, the granulation tissue is separated from the device and implanted within a body vessel of the same human, making the granulation tissue autologous relative to the human patient. Prosthetic valve devices of the present invention comprising autologous granulation tissue are more likely to avoid immunological rejection or reaction.

It should be noted that the terms "insert", "inserting", and "inserted" are used herein to refer to portions of the application generally involving the placement of an object (e.g., a cusp-forming device) in a body cavity to facilitate the formation of granulation tissue in accordance with the present invention. On the other hand, the terms "implant", "implanting", "implanted", "implantation", and "implantable" are used herein to refer to portions of the application generally involving the later placement of a prosthetic valve of the present invention in a body passageway (e.g., within a vein). Therefore, while the terms could be used to describe either scenario, they are segregated in the present application solely for the sake of clarity.

Figure 2A:
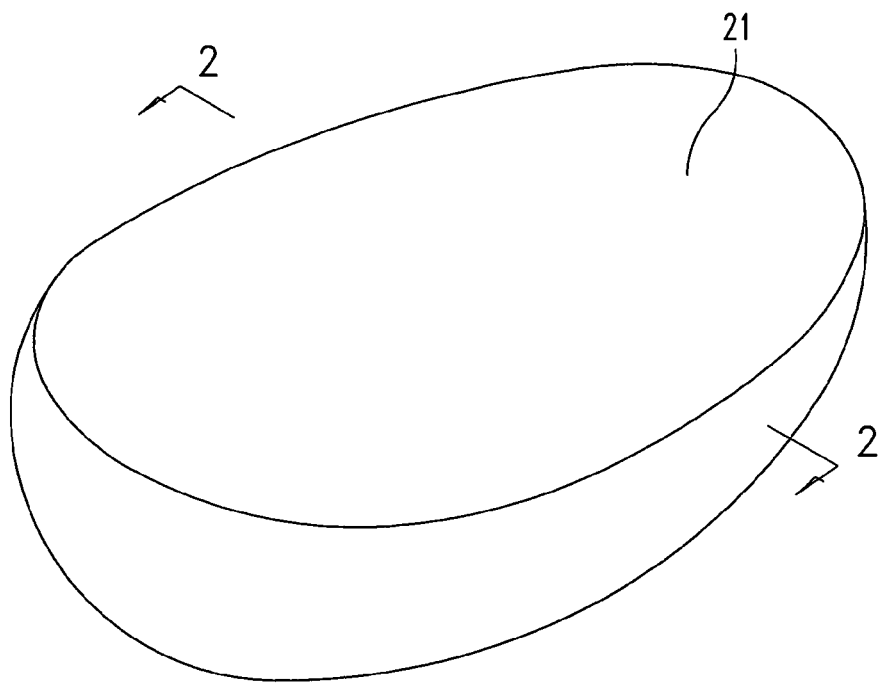
FIG. 2A provides a perspective view of a cusp-forming device of the present invention.
Figure 2B:
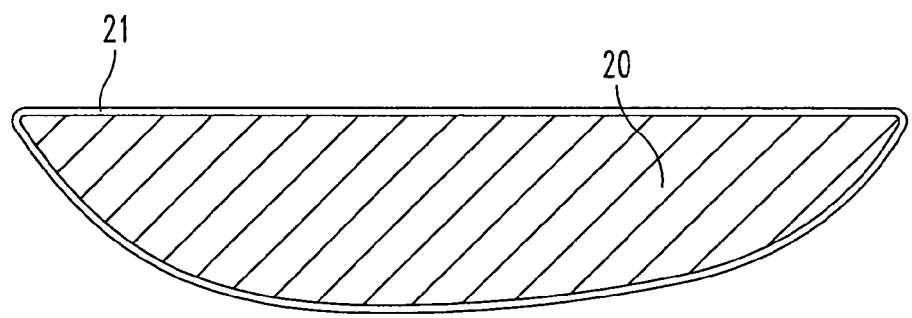
FIG. 2B provides a cross-sectional view of the device of FIG. 2A along the view line 2-2 shown in FIG. 2A.

With reference now to FIGS. 2A and 2B together, shown are a perspective view and a cross-sectional view, respectively, of an illustrative cusp-forming device 20 of the invention with granulation tissue 21 formed thereon. The size, shape, and/or configuration of the cusp-forming device 20 can be varied to provide a prosthetic cusp having any suitable dimension.

As before, the cusp-forming device 20 is inserted into a body cavity for a period of time sufficient for granulation tissue 21 to form thereon. The shape and/or configuration of the device 20 influences the shape and/or configuration of the granulation tissue 21 formed. Also, because different residence times can affect the amount and/or type of granulation tissue 21 formed, different residence time schedules can be designed through routine experimentation so as to allow for a suitable degree of granulation tissue formation. In certain embodiments, the residence time is such that the tissue material 21 is able to retain the general shape of the device 20 after being separated therefrom. Also, since the amount and/or type of granulation tissue 21 formed can affect the flexibility of the prosthetic cusp provided, different residence schedules can be designed through routine experimentation so as to allow for a suitable degree of prosthesis flexibility. After a suitable residence time, the cusp-forming device 20 is removed from the body cavity, and optionally manipulated to form an implantable prosthetic cusp.

In certain embodiments, the granulation or other tissue formed may be free of additional, non-native crosslinking, or may contain additional crosslinking. If desired, such additional crosslinking may be performed to impart further shape memory to the tissue. This additional crosslinking may be achieved by photo-crosslinking techniques, by chemical crosslinkers, or by protein crosslinking induced by dehydration or other means. When additionally crosslinked, the tissue can be additionally crosslinked internally within a single layer, and/or crosslinking may be used in whole or in part to bond multiple tissue layers to one another. Thus, additional crosslinking may be added to individual tissue layers prior to bonding to one another, during bonding to one another, and/or after bonding to one another. Nonetheless, because certain crosslinking techniques, certain crosslinking agents, and/or certain degrees of crosslinking can destroy any bioactive substances potentially present in tissue of the invention, where preservation of such substances is desired, any crosslinking of the tissue can be performed to an extent or in a fashion that allows the tissue to retain at least a portion of these bioactive substances. Chemical crosslinkers that may be used include for example aldehydes such as glutaraldehydes, diimides such as carbodiimides, e.g., 1-ethyl-3-(3-dimethylaminopropyl)carbodiimide hydrochloride, ribose or other sugars, acyl-azide, sulfo-N-hydroxysuccinamide, or polyepoxide compounds, including for example polyglycidyl ethers such as ethyleneglycol diglycidyl ether, available under the trade name DENACOL EX810 from Nagese Chemical Co., Osaka, Japan, and glycerol polyglycerol ether available under the trade name DENACOL EX 313 also from Nagese Chemical Co. Typically, when used, polyglycerol ethers or other polyepoxide compounds will have from 2 to about 10 epoxide groups per molecule.

The prosthetic cusp can be deployed within a vessel in any suitable manner. For example, in certain embodiments, the cusp is attached to walls of the vessel in an open surgery procedure. Such a procedure may comprise suturing or otherwise physically connecting portions of the cusp to the luminal surface of the vessel. Other potential attachment procedures include, for example, stapling, bonding or otherwise adhering portions of the cusp to the luminal surface of the vessel. In other embodiments, a prosthetic cusp of the invention is deployed within a vessel percutaneously, e.g., using a suitable delivery device such as a catheter. A catheter can be delivered to the treatment site using any suitable delivery technique, such as but not limited to tracking an emplaced guidewire.

Where the prosthetic cusp is to be used to provide a prosthetic venous valve, the prosthesis can be implanted above, below, or at the location of a native venous valve in the vein. In certain aspects, the native valve, or any portion thereof, is removed from the vein prior to implanting the prosthetic valve, while in other aspects, it is not. Additionally, it should be noted that a plurality of the valves can be implanted in a given vein, to treat venous insufficiency or other similar disorders.

Again, one or more prosthetic cusps of the present invention can be adapted to provide any valve suitable for implantation within a body vessel. Illustratively, a prosthetic valve device can comprise a tubular element, e.g., a tube of granulation tissue material. The tube can be manipulated, for example, by everting the tube, trimming portions of the tube, and/or incorporating objects into the tube, such as but not limited to one or more frame elements and/or one or more anchoring elements.

In certain embodiments, a cusp-forming device 20 remains part of a prosthetic valve device provided for implantation. In these embodiments, the cusp-forming device 20 may be a relatively thin, cusp-shaped piece of biodegradable matrix material. In other embodiments, a cusp-forming device 20 is associated with a biodegradable matrix material. In these embodiments, after the cusp-forming device, biodegradable matrix material, and granulation tissue are removed form the body cavity, the biodegradable matrix material and the granulation tissue, or portions thereof, can be separated from the cusp-forming device, wherein the biodegradable matrix material generally remains associated with the later implanted prosthetic valve device until it dissolves or breaks down.

The current embodiment is useful for forming unprocessed prosthetic cusps comprising isolated granulation tissue material that can later be adapted to provide any prosthetic valve device suitable for implantation within a body passageway. In this regard, the size, shape, and/or configuration of the cusp-forming device 20 may or may not be selected with a particular prosthetic valve device in mind. Accordingly, the dimensions of the cusp-forming device 20 can be varied to provide prosthetic cusps of any suitable size, shape, and/or configuration. In certain embodiments, one or more prosthetic cusp devices of the invention are adapted for implantation in a procedure occurring shortly after (e.g., within 24 hours) the prosthetic cusps are provided, while in other embodiments, one or more prosthetic cusps are sterilely packaged for later use, for example, at least 24 hours after the prosthetic cusps are provided.

Figure 3A:
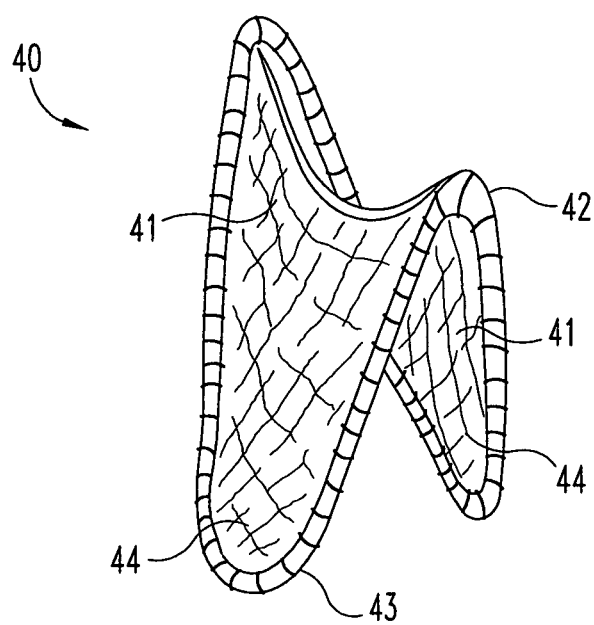
FIG. 3A provides a perspective view of a prosthetic valve of the present invention.

FIG. 3A is a perspective view of an illustrative prosthetic valve device 40 of the invention, which includes a pair of leaflets 41 attached to a frame 42, wherein the leaflets 41 comprise isolated granulation tissue material such as that described herein. The leaflets 41 can be attached to the frame 42 in any suitable manner. For example, in the illustrated embodiment, sutures 43 attach portions of the leaflets' peripheral regions to the frame 42, although it should be noted that other modes of attachment (e.g., adhesives, fasteners, tissue welding using heat and/or pressure, etc.), alone or in combination, are contemplated as well. In other embodiments, the frame 42, or portions thereof, fit into sleeves or pockets formed in peripheral regions of the leaflets 41. Such sleeves can be formed, for example, by rolling up or folding portions of the leaflets' peripheral regions and suturing the material to itself.

Figure 3B:
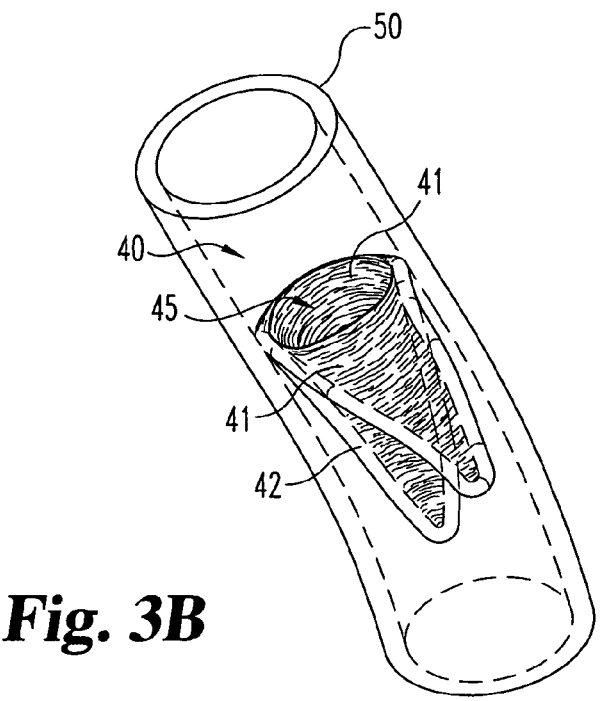
FIG. 3B provides a perspective view of the valve of FIG. 3A implanted within a body passageway, the valve in a generally open configuration.

When the valve is deployed in a body passageway (e.g., at a treatment site within the venous system), the leaflets 41 move back and forth in response to changes in fluid dynamic pressure. When fluid is stagnant or flowing through the passageway in a normal, forward direction, the leaflets 41 remain mostly open (as shown in FIG. 3B). When fluid begins to flow in a direction opposite its normal, forward flow, the leaflets 41 move toward a closed position (as shown in FIG. 3C).

Figure 3C:
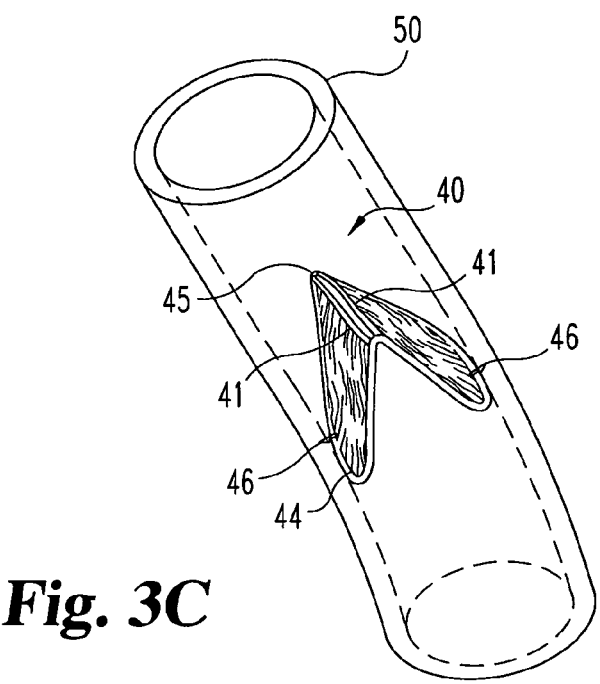
FIG. 3C provides a perspective view of the valve of FIG. 3A implanted within a body passageway, the valve in a generally closed configuration.

Although the embodiment depicted in FIGS. 3A through 3C is a bi-leaflet valve, it should again be noted that the present invention provides for prosthetic valves having one, two, three or any suitable number of leaflets. For example, bi-leaflet valves may prove advantageous in low-flow venous situations, whereas tri-leaflet embodiments, like those used to replace certain diseased heart valves, may prove advantageous in relatively higher-flow situations, although it is to be understood that the number of leaflets selected for a particular valve of the invention need not depend on the location in which the prosthesis is to be implanted.

Continuing with FIG. 3A, it should be noted that after the prosthesis is assembled, the leaflets 41 may be manipulated to alter their shape, size, configuration, and/or orientation. For example, the leaflets 41 may be chemically or otherwise treated to modify the flow dynamics within the prosthesis so that bodily fluid collecting in pockets near bottom portions 44 of the leaflets is more likely to be flushed away or continually mixed with fresher incoming fluid.

The frame 42 depicted in FIG. 3A is only one of many different types of frames that could be utilized in the present invention. Any suitable frame design or style could be used depending on the characteristics desired for a particular application, procedure, technique, and/or patient. For example, in certain embodiments, the prosthetic valve device 40 includes a collapsible frame to facilitate delivery of the valve or to provide other benefits. Such frames, or any portion thereof, may be self-expanding, or alternatively, may be forcibly expandable (e.g., balloon-expandable). In other embodiments, the prosthetic valve 40 includes one or more removable frame elements such as those previously described in relation to International Patent Application serial No. PCT/US2004/008176. Also, the frame 42 can comprise any suitable material. For example, the frame 42 could be formed with a metallic material including but not limited to stainless steel, titanium, cobalt, tantalum, gold, platinum, nickel, iron, copper and the like, as well as alloys of these metals (e.g., cobalt alloys, such as Elgiloy®, a cobalt-chromium-nickel alloy, MP35N, a nickel-cobalt-chromium-molybdenum alloy, and Nitinol®, a nickel-titanium alloy).

In addition to metallic materials, a variety of other materials can be used to form the frame 42. Illustratively, a frame material may be selected to suit a particular application (e.g., by considering weight, durability, collapsibility, etc.). In certain embodiments, a frame comprises a bioresorbable element. Further, the material could be in the form of yarns, fibers, and/or resins, monofilament yarns, high tenacity polyester. Moreover, the present application contemplates other plastic, resin, polymer, woven, and fabric surgical materials, other conventional synthetic surgical materials, such as a shape-memory plastic, and/or combinations of such materials, for forming the frame 42. Further, appropriate ceramics can be used, including, without limitation, hydroxyapatite, alumina and pyrolytic carbon.

FIGS. 3B and 3C depict certain prosthetic valve configurations for providing valve function in a body passageway. In particular, FIG. 3B provides a perspective view of valve device 40 implanted or engrafted within a vascular vessel 50, the valve in a generally open configuration. The valve 40 can be deployed within the vessel in any suitable manner, including those previously disclosed for deploying a prosthetic cusp of the invention. Also, the valve device 40 can be attached to the vessel in any suitable manner, including but not limited to those previously described. For example, the valve device can be deployed within and/or attached to the vessel percutaneously. As depicted, the leaflets 41 are configured to move toward and away from one another to close and open, respectively, the valve orifice 45. FIG. 3C provides a perspective view of the valve of FIG. 3A in a generally closed configuration.

The prosthetic valve device 40 can include at least one anchoring element 46 (e.g., a barb) to hold the device at a general location within a vessel. Therefore, while the leaflets 41 are provided to move within the vessel to perform a valving function, the at least one anchoring element 46 generally prevents the valve 40 as a whole from migrating from the implantation site. The at least one anchoring element 46 can be incorporated into or attached to the valve device 40 in any suitable manner, including but not limited to suturing, gluing, and the like. Also, suitable anchoring elements can comprise any object, device, or material suitable to attach a valve device to a vessel wall. For example, in certain embodiments, an anchoring element incorporates an adhesive, while in other embodiments, an anchoring element comprises one or more tissue-penetrating attachment elements, such as but not limited to hooks, microbarbs, spurs, claws, prongs, and the like.

Further in this regard, the at least one anchoring element 46 can have any suitable shape, size, and/or orientation to suitably anchor the valve device 40 within the vessel 50. For example, the at least one anchoring element 46 can adopt a curved configuration and/or can have adaptations to cause it to resist withdrawal from a tissue structure once attached thereto, e.g. in the case of a fish hook-type structure embedded or partially embedded within a vessel wall.

Similarly, the at least one anchoring element 46 can be formed with any suitable biocompatible material, and in some embodiments is formed with a bioresorbable material. In certain other embodiments, the at least one anchoring element 46 is formed with a rigid or semi-rigid synthetic polymeric material, including but not limited to polytetrafluoroethylene (PTFE) (including expanded PTFE) and/or polyethylene terephthalate (PET). In other embodiments, an anchoring element is formed with a rigid or semi-rigid metallic material, including but not limited to, stainless steel, titanium, cobalt, tantalum, gold, platinum, nickel, iron, copper and the like, as well as alloys of these metals (e.g., cobalt alloys, such as Elgiloy®, a cobalt-chromium-nickel alloy, MP35N, a nickel-cobalt-chromium-molybdenum alloy, and Nitinol®, a nickel-titanium alloy). In still other embodiments, an anchoring element is formed with an appropriate ceramic material, including, without limitation, hydroxyapatite, alumina and pyrolytic carbon. Further in this regard, an anchoring element of the invention can include a radiopaque material for positioning and monitoring the prosthetic valve device within a patient.

A prosthetic valve device of the invention can be constructed so as to have predetermined dimensions. For example, a valve device can be adapted to provide a valve function in a vein or other vessel of a specific diameter. In certain embodiments, the dimensions of the device can be selected so as to render the device suitable for providing a valve function in a vein or other vessel having an inner diameter of about 5 mm to about 25 mm, more typically in the range of about 8 mm to about 20 mm.

The invention also provides a prosthetic valve device product line. In certain embodiments, a prosthetic valve device product line comprises a plurality of packaged, sterile valve devices such as those described herein, wherein the plurality of valve devices includes packaged valves of varying dimensions to suit varying patients or applications. For example, a product line including at least 3 differently dimensioned products, more typically about 3 to about 20 differently dimensioned products, is contemplated as within the scope of the present invention.

Prosthetic valve devices of the present invention are desirably adapted for deployment within the vascular system, and in certain preferred embodiments, are adapted for deployment within the venous system. Accordingly, a valve, such as valve 40, can be adapted as a venous valve, for example, for attachment within veins of the legs or feet, to treat venous insufficiency.

The present invention also provides, in certain aspects, a line of medical products, wherein a medical product of the invention includes one or more prosthetic valve devices of the invention in a sealed package. When a plurality of valves is included, the valves can each be of substantially the same size and shape, or, alternatively, can vary with respect to size and shape.

Figure 4:
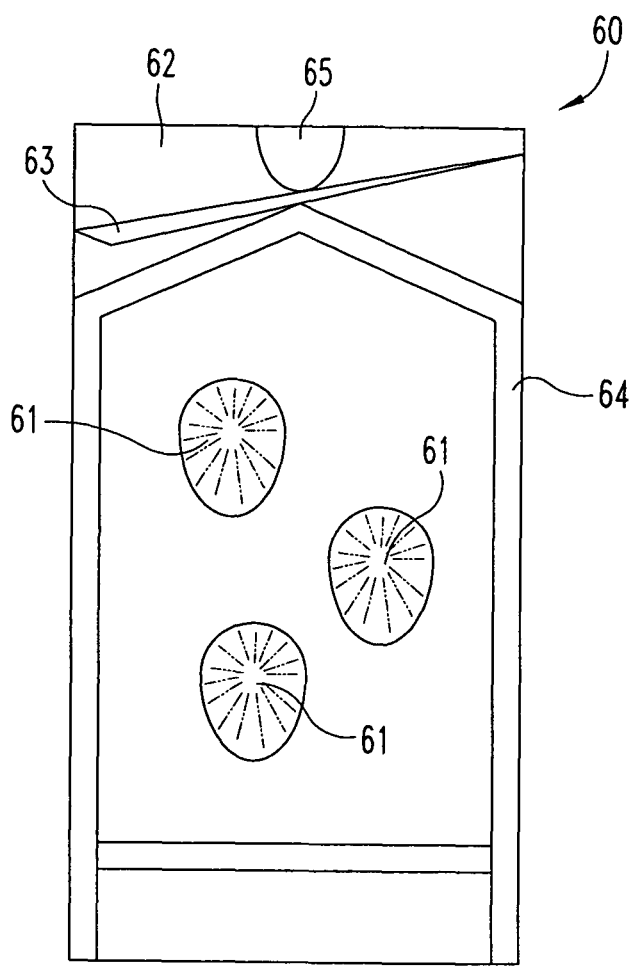
FIG. 4 provides a top view of a medical product of the present invention.

With reference now to FIG. 4, shown is a top view of an illustrative medical product 60 of the present invention that includes three prosthetic cusps 61 sealed within sterile medical packaging, the cusps 61 comprising isolated granulation tissue material. In particular, medical product 60 has packaging including a backing layer 62 and a front film layer 63 (shown partially drawn away from backing layer 62). The cusps 61 are sealed between backing layer 62 and film 63 utilizing a boundary of pressure-adhesive 64 as is conventional in medical packaging. A cut-out 65 may be provided in the backing layer 62 to assist a user in separating the film layer 63 from the backing layer 62.

Sterilization of the medical product 60 may be achieved, for example, by irradiation, ethylene oxide gas, or any other suitable sterilization technique, and the materials and other properties of the medical packaging will be selected accordingly. Also, isolated granulation tissue material of the invention can be contained in a sterile packaging in any suitable state. Suitable states include, for example, a hydrated or dehydrated state. The isolated granulation tissue material can be dehydrated by any means known in the art (e.g., lyophilization or air dried). If isolated granulation tissue material of the present invention is stored in a dehydrated state, it is preferred that it retains all of its biological and mechanical properties (e.g., shape, density, flexibility, etc.) upon rehydration.

Additionally, the package can include indicia to communicate the contents of the package to a person, machine, computer, and/or electronic device. Such indicia may include the dimensions of, the type of materials used to form, and/or the physical state of, the contents of the package. In certain embodiments, the cusps or valves are packaged for sale with instructions for use. For example, in certain preferred embodiments, a medical product includes at least one prosthetic vascular valve sealed within a sterile package, wherein the packaging can have visible indicia identifying the at least one valve as a venous or other vascular valve, and/or can contain or otherwise be associated with printed materials identifying the contents as a venous or other vascular valve and including information concerning its use as a venous or other vascular valve. The packaging could also include visible indicia relating to the dimension of the at least one valve, and/or relating to the vessel diameter(s) for which the at least one valves is configured.

The present invention also provides, in certain aspects, the insertion of one or more cusp-forming devices into a body cavity as a step in providing one or more implantable prosthetic valve devices in accordance with the present invention.

All publications and patent applications cited in this specification are herein incorporated by reference as if each individual publication or patent application were specifically and individually indicated to be incorporated by reference. Further, any theory, mechanism of operation, proof, or finding stated herein is meant to further enhance understanding of the present invention, and is not intended to limit the present invention in any way to such theory, mechanism of operation, proof, or finding. While the invention has been illustrated and described in detail in the drawings and foregoing description, the same is to be considered as illustrative and not restrictive in character, it being understood that only selected embodiments have been shown and described and that all equivalents, changes, and modifications that come within the spirit of the inventions as defined herein or by the following claims are desired to be protected.

What is claimed is:

1. An implantable valve for modifying fluid flow in a body passageway, said valve comprising a frame and at least one valve cusp attached to the frame, the at least one valve cusp having a wall of material in a cusp shape with a first, concave exposed surface and a second, convex exposed surface opposite the first exposed surface, and a wall thickness spanning from said first exposed surface to said second exposed surface, wherein said wall of material consists of isolated granulation tissue grown to and retaining shape memory for said cusp shape, and wherein said isolated granulation tissue is free of additional, non-native crosslinking.

2. The valve of claim 1, wherein said isolated granulation tissue includes mesothelial cells.

3. The valve of claim 1, wherein said isolated granulation tissue includes myofibroblasts.

4. The valve of claim 1, wherein said isolated granulation tissue is decellularized.

5. The valve of claim 1, wherein said isolated granulation tissue is formed in a body cavity.

6. The valve of claim 5, wherein said body cavity is in a human.

7. The valve of claim 5, wherein said body cavity is in a human patient to receive said implantable valve.

8. The valve of claim 1 which is a monocusp valve.

9. The valve of claim 1 which is a multicuspid valve.

10. The valve of claim 1 which is a bicuspid valve.

11. The valve of claim 1 which is a tricuspid valve.

12. The valve of claim 1 configured for implantation as a vascular valve.

13. The valve of claim 1 configured for implantation as a heart valve.

14. The valve of claim 1 configured for implantation as a venous valve.

15. The valve of claim 1, wherein said cusp shape curves in both a longitudinal direction and a lateral direction along said valve cusp.

16. The valve of claim 1, wherein said at least one valve cusp is sutured to said frame.

17. The valve of claim 16, wherein said frame is collapsible.

18. The valve of claim 16, wherein said frame is bioresorbable.

19. The valve of claim 16, wherein said frame comprises a metallic material.

20. The valve of claim 1, wherein said valve includes adaptations to attach said valve to walls of said body passageway.

21. The valve of claim 1, wherein the wall thickness of the entire valve cusp is formed from isolated granulation tissue.

22. A method of treatment comprising implanting at least one implantable valve according to claim 1 within a body passageway of a patient.

23. The method of claim 22, wherein the at least one valve is implanted within a vascular vessel to treat a condition of the vascular system.

24. The method of claim 22, wherein the at least one valve is implanted within a vein to treat venous insufficiency.

25. The method of claim 22, wherein the at least one valve is implanted percutaneously.

26. The method of claim 22, wherein the wall thickness of the entire valve cusp is formed from isolated granulation tissue.

27. The method of claim 22, wherein said isolated granulation tissue has not been treated with a chemical crosslinking agent.

* * * * *